United States Patent [19]

Wilner

[11] Patent Number: 4,704,380

[45] Date of Patent: Nov. 3, 1987

[54] METHOD OF STIMULATING THE GROWTH OF MACROPHAGE-LIKE CELLS UTILIZING MITOGENIC PEPTIDES

[75] Inventor: George D. Wilner, St. Louis, Mo.

[73] Assignee: Washington University, St. Louis, Mo.

[21] Appl. No.: 928

[22] Filed: Jan. 7, 1987

Related U.S. Application Data

[62] Division of Ser. No. 787,411, Oct. 15, 1985.

[51] Int. Cl.$^4$ ............................................. A61K 37/02
[52] U.S. Cl. ................................... 514/14; 514/885; 424/101
[58] Field of Search ................... 514/14, 885; 424/101

[56] References Cited

U.S. PATENT DOCUMENTS 4,376,071  3/1983  Jennings et al. ................... 530/417

OTHER PUBLICATIONS

Bar-Shavit et al., "Identification of a Thrombin Sequence with Growth Factor Activity on Macrophages" *Proc Natl Acad Sci USA* vol. 83, pp. 976–980, Feb. 1980.
Perdue, J. Biol. Chem. 256, 2767–2776 (1981).
Bar-Shavit et al., J. Cell Biol. 96, 282–285 (1983).
Bar-Shavit et al., Science 220, 728–730 (1983).
Bar-Shavit et al., J. Cell Biol. 97, 396a, Abstract 1494 (1983).
Bar-Shavit et al., J. Cell Biol. Chem. 252, 4942–4957 (1977).
Butkowski et al., J. Biol. Chem. 252, 4942–4957 (1977).
Bar-Shavit et al., Biochemistry 23(3) 397–400 (1984).

*Primary Examiner*—John Kight
*Assistant Examiner*—Nathan M. Nutter
*Attorney, Agent, or Firm*—Scott J. Meyer; James W. Williams, Jr.

[57] ABSTRACT

Novel tetradecapeptides having the following sequence were found to have potent mitogenic activity for machropage-like cells:

H-Tyr-Pro-Pro-X-Asn-Lys-Asn-Phe-Thr-Glu-Asn-Asp-Leu-Leu-OH, wherein X=Trp or Tyr, or the physiologically acceptable salts, esters or amides thereof.

3 Claims, 2 Drawing Figures

METHOD OF STIMULATING THE GROWTH OF MACROPHAGE-LIKE CELLS UTILIZING MITOGENIC PEPTIDES

This is a division of application Ser. No. 787,411 filed Oct. 15, 1985.

BACKGROUND OF THE INVENTION

This invention relates to novel peptides having mitogenic activity for macrophage-like cells.

It is known that thrombin has a multiplicity of effects on cells. Thus, in addition to clotting fibrinogen and enzymatically activating other factors in the plasma-clotting system, it has been reported that thrombin has mitogenic activity in a variety of fibroblast cell lines in tissue culture. See, e.g., Perdue et al., *J. Biol. Chem.* 256, 2767-2776 (1981). Its function as a growth stimulator for fibroblasts is intimately linked to its esterolytic activity.

Thrombin also more recently has been described to have chemotactic activity in human peripheral blood monocytes. Bar-Shavit et al., *J. Cell Biol.* 96, 282-285 (1983).

Attempts have been made to identify the domain or domains of thrombin which are responsible for its various biological activities. Thus, Bar-Shavit et al, *Science* 220, 728-730 (1983), conclude that the chemotactic activity is mediated through a specific region on the thrombin molecule that is independent of the sites required for esterolytic activity and fibrinogen recognition. The significance of the chemotactic function is that it may be an important physiological stimulator of inflammatory responses at sites of tissue injury. This chemotactic function which involves the directional locomotion of cells is to be distinguished from a mitogenic function which is a growth factor activity in cells, i.e., a factor which stimulates the division and differentiation of cells. It has been suggested heretofore that thrombin can also elicit a mitogenic effect on macrophage-like cells. Bar-Shavit et al., *J. Cell Biol.* 97, 396a, Abstract 1494 (1983).

BRIEF DESCRIPTION OF THE INVENTION

It has now been found in accordance with the present invention that certain tetradecapeptide homologs of the human thrombin β chain are potent mitogens for macrophage-like cells. These mitogenic peptides have the following amino acid sequence:

H-Tyr-Pro-Pro-X-Asn-Lys-Asn-Phe-Thr-Glu-Asn-Asp-Leu-Leu-OH, wherein X=Trp or Tyr, or the physiologically acceptable salts, esters or amides thereof.

In the peptide structures shown herein, the amino acid components are designated by conventional abbreviations as follows:

| Amino Acid | Abbreviated Designation |
|---|---|
| L-Alanine | Ala or A |
| L-Arginine | Arg or R |
| L-Asparagine | Asn or N |
| L-Aspartic Acid | Asp or D |
| L-Cysteine | Cys or C |
| L-Glutamic Acid | Glu or E |
| L-Glutamine | Gln or Q |
| Glycine | Gly or G |
| L-Histidine | His or H |

-continued

| Amino Acid | Abbreviated Designation |
|---|---|
| L-Isoleucine | Ile or I |
| L-Leucine | Leu or L |
| L-Lysine | Lys or K |
| L-Methionine | Met or M |
| L-Phenylalanine | Phe or F |
| L-Proline | Pro or P |
| L-Serine | Ser or S |
| L-Threonine | Thr or T |
| L-Tryptophan | Trp or W |
| L-Tyrosine | Tyr or Y |
| L-Valine | Val or V |

Peptide I, which has the amino acid sequence:

H-Tyr-Pro-Pro-Trp-Asn-Lys-Asn-Phe-Thr-Glu-Asn-Asp-Leu-Leu-OH, represents residues 367-380 of the human thrombin B chain (or residues 96-109 of the human prethrombin 2 sequence). The sequence of human prethrombin 2 has been reported by Butkowski et al., *J. Biol. Chem.* 252, 4942-4957 (1977). In deriving the primary structure of human prethrombin 2, Butkowski et al. prepared certain chymotryptic peptide fragments of the cyanogen bromide cleavage product of prethrombin 1, one of which fragments corresponds to residues 95-109 of prethrombin 2. However, no biological activity was assigned to this fragment nor was the 96-109 fragment of the present invention prepared or suggested.

Peptide II, which has the amino acid sequence:

H-Tyr-Pro-Pro-Tyr-Asn-Lys-Asn-Phe-Thr-Glu-Asn-Asp-Leu-Leu-OH, is an analog of peptide I in which tyrosine is substituted for tryptophan.

Surprisingly, the novel tetradecapeptides of this invention exhibited potent mitogenic activity for macrophage-like cells whereas the following two fragments thereof were inactive:

Peptide III: H-Thr-Glu-Asn-Asp-Leu-Leu-OH

Peptide IV: H-Asn-Lys-Asn-Phe-Thr-Glu-Asn-Asp-Leu-Leu-OH

These findings suggest that the amino-terminal portion of peptides I or II are important for the mitogenic activity of the peptides of the present invention.

DETAILED DESCRIPTION OF THE INVENTION

While the specification concludes with claims particularly pointing out and distinctly claiming the subject matter regarded as forming the present invention, it is believed that the invention will be better understood from the following detailed description of preferred embodiments taken in connection with the accompanying drawings in which:

Figure 1:
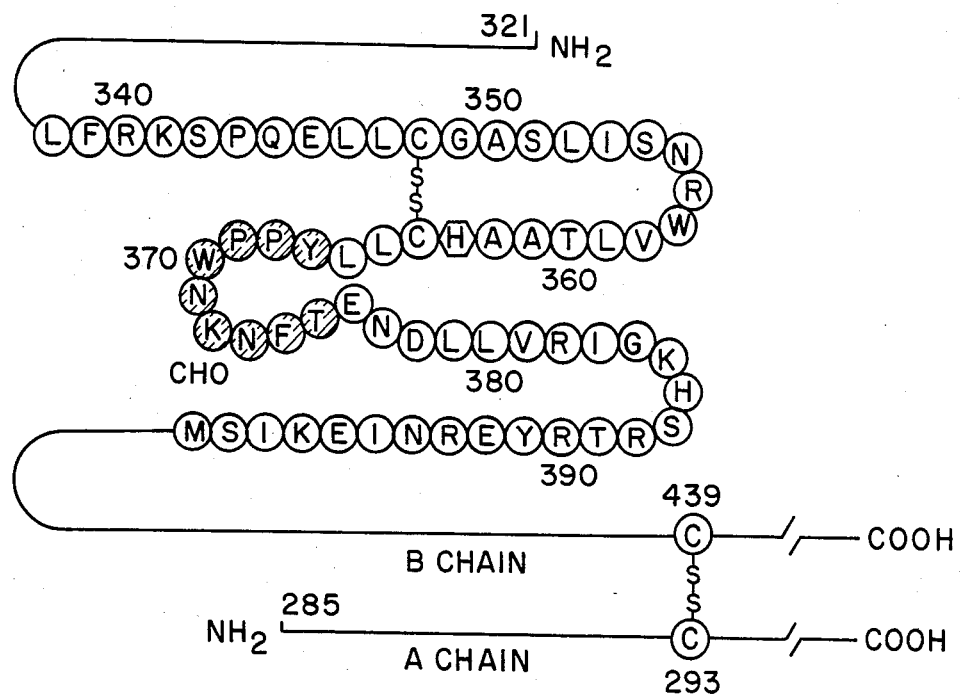
FIG. 1 is a model of human α-thrombin structure.

The model of human α-thrombin in FIG. 1 is based on the protein nomenclature of prothrombin, a single chain zymogen, which is subsequently activated and cleaved into a two chain structure at residues 272 and 321 by Factor Xa. The active enzyme so produced deletes the first 13 residues of the A chain at residue 285 by an autocatalytic event, yielding α-thrombin. The structure of peptide CB67–129 is shown, with the "loop B" insertion sequence (i.e., residues 367-375) indicated by crosshatching. The locations of active site His 363 (hexagon) and carbohydrate attachment site (at Asn 373), important structural features of this fragment, are also indicated. The amide assignment on Asx 355 and 371 is uncertain as is the precise limits of the "loop B" thrombin B chain insertion sequence.

The novel mitogenic peptides of this invention can be made by appropriate adaptation of conventional methods for peptide synthesis. Thus, the peptide chain can be prepared by a series of coupling reactions in which the constituent amino acids are added to the growing peptide chain in the desired sequence. The use of various N-protecting groups, e.g., the carbobenzyloxy group or the t-butyloxycarbonyl group (BOC), various coupling reagents, e.g., dicyclohexylcarbodiimide or carbonyldimidazole, various active esters, e.g., esters of N-hydroxypthalimide or N-hydroxysuccinimide, and various cleavage reagents, e.g., trifluoroacetic acid, HCL in dioxane, boron tris(trifluoroacetate) and cyanogen bromide, and reaction in solution with isolation and purification of intermediates is well-known classical peptide methodology.

Preferably, the peptides of this invention are prepared by the well-known Merrifield solid support method. See Merrifield, *J. Amer. Chem. Soc.* 85, 2149–54 (1963) and *Science* 150, 178–85 (1965). This procedure, though using many of the same chemical reactions and blocking groups of classical peptide synthesis, provides a growing peptide chain anchored by its carboxyl terminus to a solid support, usually crosslinked polystyrene or styrene-divinylbenzene copolymer. This method conveniently simplifies the number of procedural manipulations since removal of the excess reagents at each step is effected simply by washing of the polymer.

The general reaction sequence for conventional Merrifield peptide synthesis can be illustrated as follows:

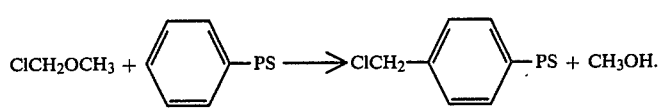

Chloromethylation step to provide reactive group for attachment of peptide, wherein PS = Polystyrene Residue.

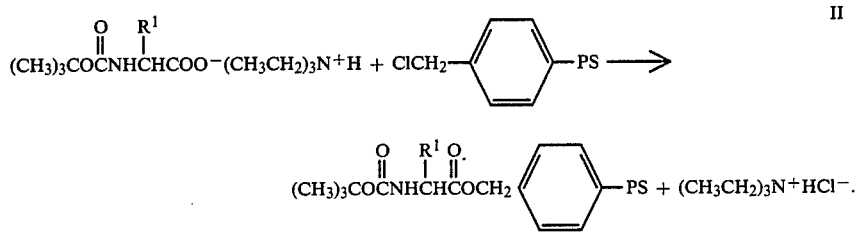

Esterification Step - Reaction with Triethylammonium salt of the First Protected Amino Acid ($R^1$) Using t-BOC Protecting Group.

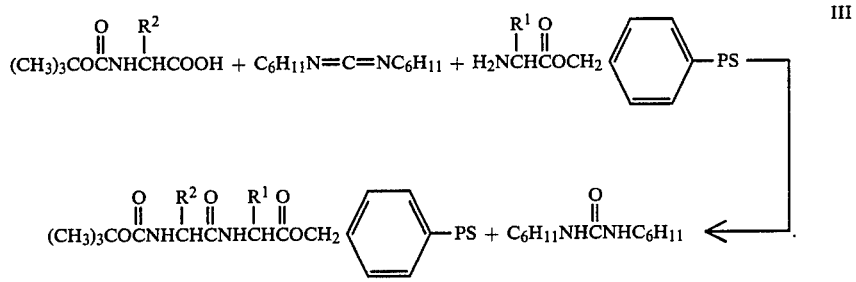

Peptide forming step with Dicyclohexylcarbodiimide Coupling Agent.

This step III follows cleavage of t-BOC such as by treatment, for example, with 25% trifluoroacetic acid in methylene chloride and liberation of N-terminal amine by excess of triethylamine, thereby enabling it to react with the activated carboxyl of the next protected amino acid ($R^2$). A final step involves cleavage of the completed peptide from the PS resin such as by treatment, for example, with anhydrous HF in anisole.

Further background information on the established solid phase synthesis procedure can be had by reference to the treatise by Stewart and Young, "Solid Phase Peptide Synthesis," W. H. Freeman & Co., San Francisco, 1969, and the review chapter by Merrifield in *Advances in Enzymology* 32, pp. 221–296, F. F. Nold, Ed., Interscience Publishers, New York, 1969; and Erickson and Merrifield, *The Proteins*, Vol. 2, p. 255 et seq. (ed. Neurath and Hill), Academic Press, New York, 1976.

The growth stimulation of macrophage-like cells can be determined by measuring the thymidine uptake of the cells at varying concentrations of the mitogenic peptides of the present invention. This was determined for several macrophage-like cell lines including J774, P388D1, RAW and PU5. These are well-known murine cell lines available, for example, from the American Type Culture Collection, Rockville, Md.

The following examples will further illustrate the invention although it will be appreciated that the invention is not limited to these specific examples.

EXAMPLE 1

Peptide I, H-Tyr-Pro-Pro-Trp-Asn-Lys-Asn-Phe-Thr-Glu-Asn-Asp-Leu-Leu-OH, representing residues 367–380 of the human thrombin B chain, and containing the loop B insertion sequence as shown in FIG. 1, was synthesized by a modification of the conventional Merrifield solid phase peptide synthesis, as described by Wilnert et al., *Biochemistry* 15(6), 1209–1213 (1976) and 18 (23), 5078–5082 (1979). The fully protected peptide was simultaneously deprotected and cleaved from its resin support by the two-step HF catalyzed $S_N2$ procedure of Tam et al., *J. Am. Chem. Soc.* 105, 6442–6455 (1983). The crude peptide was definitively purified by ion exchange chromatography on a DEAE-Sephacel ® column by the method described by Wilner et al., *Biochemistry* 15(6), 1209–1213 (1976). Peptide purity was ascertained by reversed-phase $C_{18}$ high performance liquid chromatography (HPLC) according to procedure described by Fulmer et al., *J. Biol. Chem.* 254, 7208–7212 (1979), where it chromatographed as a single peak. The peptide was also found to be homogeneous by thin layer chromatography (TLC), migrating as a single spot using two different solvent systems. Amino acid analysis yielded molar ratios consistent with the desired peptide sequence.

In this peptide synthesis, all components were of reagent grade. $N^\alpha$-tert-Butoxycarbonyl (BOC) L-amino acids were purchased from Bachem, Inc., Torrance, CA. BOC amino acids with protected side chains were γ-benzylglutamic acid, β-benzylaspartic acid, O-benzylthreonine, 2-chlorobenzyloxycarbonyl-L-lysine, N-formyltryptophan, and O-benzyltyrosine. Asparagine was introduced unprotected by direct coupling with dicyclohexylcarbodiimide in the presence of equimolar 1-hydroxybenzotriazole. Purity of the BOC amino acids was assessed by melting points (uncorrected) and thin-layer chromatography. DEAE-Sephacel was obtained from Pharmacia Fine Chemicals, Piscataway, N.J. Bio-Gel ® P-2 (200–400 mesh) was purchased from Bio-Rad Laboratories, Rockville Centre, NY. Styrene-divinlybenzene beads, 1% cross-linked, 200–400 mesh, chlormethylated (1.16 mequiv of Cl per g)., were purchased from Lab Systems, Inc., San Mateo, CA, and were extracted with warm (60° C.) dimethylformamide for 18 hours prior to use.

In the peptide synthesis, esterification of the COOH-terminal residue to the insoluble support was accomplished by neutralization of this residue (i.e., leucine) with tetramethylammonium hydroxide, and reacting the component $N^\alpha$-tert-BOC-L-leucine tetramethylammonium salt with the chloromethylated resin in dimethylsulfoxide (DMSO) at 80° for one hour. Amino group deprotection was accomplished using 25% trifluoroacetic acid in methylene chloride and neutralization was performed using 10% triethylamine in methylene chloride. All residue couplings were performed in methylene chloride using dicyclohexylcarbodiimide (4 molar excess of reagents), and couplings were monitored using the Kaiser (Ninhydrin) test, and terminated (if necessary) using N-acetylimidazole. The completed, fully protected peptide was cleaved from its insoluble support and deprotected by the two-step HF-catalyzed $S_N2$ procedure as stated above.

Following washing of the resin with dry ethyl ether, the crude peptide was extracted in 10% acetic acid and lyophilized. The peptide was simultaneously desalted and definitively purified on a DEAE-Sephacel column and eluted with linear salt gradients developed in a varigrad device (Buchler Instruments, Inc., Fort Lee, N.J.). The starting buffer was 0.05 M sodium borate, and the limit buffer was the starting buffer containing additionally 0.5 M sodium chloride. Column dimensions were 1.2×40 cm. Eluate fractions were analyzed by absorbance at 225 nM, and by thin-layer chromatography using glass plates pre-coated with silica gel G (Merck Darmstadt, Germany). Fluorescamine and chlorine: o-tolidine sprays were used for peptide visualization. The two solvent systems used for thin-layer chromatography were (1) 1-butanol-acetic acid-water (1:1:1, v/v/v) and
(2) ethyl acetate-pyridine-acetic acid-water (5:5:1:3, v/v/v/v).

The desired peptide eluted as the dominant peak. This peak was subsequently desalted on a 2.5×100 cm Bio-Gel P-2 column using a 0.5 M ammonium bicarbonate buffer. HPLC analysis of this peptide using a reversed-phase $C_{18}$ column showed the peptide to be homogeneous. This peptide also gave the expected molar ratios on amino acid analysis.

EXAMPLE 2.

Peptide II, H-Tyr-Pro-Pro-Tyr-Asn-Lys-Asn-Phe-Thr-Glu-Asn-Asp-Leu-Leu-OH, was prepared according to the procedure of Example 1 except that an equimolar amount of BOC-tyrosine was substituted for BOC-tryptophan in the solid phase synthesis.

EXAMPLE 3

To determine the mitogenic effects of the purified tetradecapeptide I of Example 1 on macrophage-like cells, the following tests were carried out.

$^3[H]$-TdR incorporation. Various cell lines were plated in Dulbeccos's Modified Eagle Medium (DMEM) containing 10% fetal calf serum (FCS) in 95% $CO_2$ humidified atmosphere at 37° C. at an initial density of $5\times10^5$ per well in 24 well disposable plastic plates (Falcon, Oxnard, Calif.). Arrest of DNA synthesis (i.e., $G_0/G_1$) was achieved by incubating the cells for 48 hours in serum-free DMEM containing 0.1% bovine serum albumin (BSA). The cells were then exposed to the peptide or to various thrombin forms, or to FCS for 48 hours. Enhanced thymidine incorporation was assessed following a 2 hour pulse of N-methyl$^3[H]$-TdR (1 μCi/ml). The cells were washed ×3 in PBS (phosphate buffered saline, pH 7.4) at 4, precipitated with 10% trichloroacetic acid (30 min at 4) and the insoluble material extracted ×2 with ETOH:$ET_2O$ (3:1 v/v). The precipitate was solubilized in N NaOH and aliquots withdrawn for protein determinations using a dye-binding assay (Bio Rad Labs., Richmond, Calif.) and liquid scintillation spectrometry.

Figure 2:
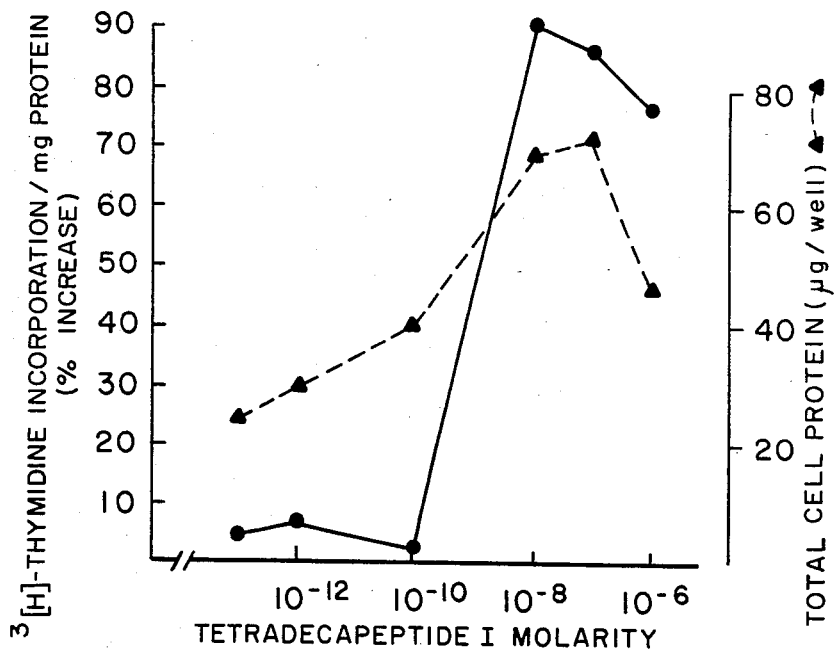
FIG. 2 is a graphical representation of the thymidine incorporation by J774 murine macrophage-like cells and total cell protein levels following exposure of the cells to a synthetic mitogenic peptide in one embodiment of the invention.

The various cell lines employed in these tests were the murine macrophage-like cell lines J774, P388D1, RAW and PU5. The various thrombin forms used in these tests were platelet-derived growth factor (PDGF), epidermal growth factor (EGF), fibroblast growth factor (FGF), and nerve growth factor (NGF). For background information on these known polypeptide growth factors see, for example, the recent review article by Kris et al., *Biotechnology*, February 1985, pp. 135-140; and the comprehensive review in *Hormonal Proteins and Peptides*, Ed. by Choh Hao Li, Vol. 12, "Growth Factors," Academic Press, 1984. EGF, NGF and FGF are commercially available from Biomedical Technologies, Cambridge, Massachusetts. In a representative test, 24 hours following exposure of the growth-arrested cells to optimal concentrations of the peptide (i.e., $10^{-8}$ M), cell numbers increased approximately two-fold from a control value of $1.2633\ 2\times 10^5$ cells/culture well. By way of comparison, the known growth promoting agents PDGF, EGF, NGF and FGF failed to elicit proliferation of these cells at concentration ranges of up to 500 ng/ml. The results are set forth in FIG. 2 and in Table I, below. In FIG. 2, the baseline tritiated thymidine ($^3$[H]-TdR) incorporation in quiescent J774 cells was 5000 cpm ± 420 s.e.m. (standard error of the mean) per well. The results are expressed as the mean of triplicate determinations.

TABLE I

| | | | |
|---|---|---|---|
| Mitogenic Stimulation of Growth-Arrested Macrophage-like Tumor Cell Lines | | | |
| Cells | Mitogen | Conc./Well[b] | $^3$[H]—TdR Incorporation/mg/Protein (% Increase)[c] |
| (1) J774 | Peptide | $10^{-8}$ M | 140 ± 8.5 |
| J774 | PDGF[a] | >500 ng | 9.4 ± 0.3 |
| J774 | EGF[a] | >500 ng | 5.2 ± 0.2 |
| J774 | FGF[a] | >500 ng | 0 ± 0.4 |
| J774 | NGF[a] | >500 ng | 0 ± 0.5 |
| (2) J774 | Peptide | $10^{-8}$ M | 190 ± 12 |
| P388D1 | Peptide | $10^{-7}$ M | 226 ± 22 |
| RAW | Peptide | $10^{-8}$ M | 276 ± 18 |
| PU5 | Peptide | $10^{-6}$ M | 112 ± 4.4 |

[a]These preparations stimulated > 4-fold increase in $^3$[H]—TdR incorporation in quiescent HF cells at the concentration shown. Baseline incorporation in unstimulated cells was 280 cpm ± 21 s.e.m. per well.
[b]Concentration yielding optimal specific $^3$[H]—TdR incorporation is shown. Where stimulation was not significantly greater than control (i.e., > 1.5-fold), highest concentration tested is indicated.
[c]$^3$[H]—TdR incorporation was determined as set forth above. Each value represents the mean percent increase ± s.e.m. from triplicate cultures in a representative test. Comparable data was obtained in at least 3 independent tests. Underlined values indicate significant stimulation.

Various other examples will be apparent to the person skilled in the art after reading the present disclosure without departing from the spirit and scope of the invention and it is intended that all such examples be included within the scope of the appended claims.

What is claimed is:

1. The method of stimulating the growth of macrophage-like cells comprising subjecting said cells to a growth stimulating amount of a peptide comprising the following amino acid sequence H-Tyr-Pro-Pro-X-Asn-Lys-Asn-Phe-Thr-Glu-Asn-Asp-Leu-Leu-OH, wherein X=Trp or Tyr, or the physiologically acceptable salts, esters or amides thereof.

2. The method of claim 1 in which X is Trp.
3. The method of claim 1 in which X is Tyr.

* * * * *